United States Patent
Stupperich et al.

(10) Patent No.: US 7,544,628 B2
(45) Date of Patent: Jun. 9, 2009

(54) LOOP-FORMING NONWOVEN MATERIAL FOR A MECHANICAL CLOSURE ELEMENT

(75) Inventors: Hans-Peter Stupperich, Heidenheim (DE); Fridmann Hornung, Lauchheim (DE); Ruediger Kesselmeier, Herbrechtingen (DE)

(73) Assignee: Paul Hartmann AG, Heidenheim (DE)

( * ) Notice: Subject to any disclaimer, the term of this patent is extended or adjusted under 35 U.S.C. 154(b) by 0 days.

(21) Appl. No.: 11/664,721

(22) PCT Filed: Oct. 27, 2005

(86) PCT No.: PCT/EP2005/011492

§ 371 (c)(1),
(2), (4) Date: Apr. 5, 2007

(87) PCT Pub. No.: WO2006/048173

PCT Pub. Date: May 11, 2006

(65) Prior Publication Data

US 2008/0026178 A1    Jan. 31, 2008

(30) Foreign Application Priority Data

Nov. 3, 2004   (DE) ................ 10 2004 053 469

(51) Int. Cl.
*D04H 1/00* (2006.01)
*B32B 3/06* (2006.01)
*A44B 18/00* (2006.01)

(52) U.S. Cl. .............. 442/327; 428/99; 428/100; 428/195.1; 428/223; 24/442; 24/443; 24/444; 24/445; 24/446

(58) Field of Classification Search ............. None
See application file for complete search history.

(56) References Cited

U.S. PATENT DOCUMENTS

| 4,088,726 | A | * | 5/1978 | Cunbers ............... 264/123 |
| 5,722,968 | A | * | 3/1998 | Datta et al. .......... 604/391 |
| 5,763,041 | A | * | 6/1998 | Leak et al. ........... 428/100 |
| 6,093,665 | A | * | 7/2000 | Sayovitz et al. ...... 442/394 |
| 6,713,159 | B1 |  | 3/2004 | Blenke |
| 2004/0163221 | A1 |  | 8/2004 | Shepard |

FOREIGN PATENT DOCUMENTS

| DE | 88 01 667 | 5/1988 |
| DE | 94 22 363 | 11/2000 |
| DE | 199 20 804 | 2/2003 |
| DE | 699 08 102 | 2/2004 |
| EP | 1 302 582 | 4/2003 |
| JP | 10211236 | 8/1998 |
| WO | WO 00/37249 | 6/2000 |

* cited by examiner

*Primary Examiner*—Elizabeth M Cole
*Assistant Examiner*—Jennifer Steele
(74) *Attorney, Agent, or Firm*—Paul Vincent (57) ABSTRACT

A loop-forming nonwoven material (28) is used as a mechanical closure element, in particular for disposable sanitary articles (2) such as various types of nappies, incontinence articles and pads. A first upper face (40) of the nonwoven material (30) has first larger non-bonded areas (42), which are located at a distance from one another in the form of islands. The first larger non-bonded areas (42) of the nonwoven material are delimited by bonded contours (44) and surrounded by second smaller non-bonded areas (48) lying outside said delimitation and separating the larger areas from one another.

25 Claims, 7 Drawing Sheets

LOOP-FORMING NONWOVEN MATERIAL FOR A MECHANICAL CLOSURE ELEMENT

This application is the national stage of PCT/EP2005/011492 filed on Oct. 27, 2005 and also claims Paris Convention priority of DE 10 2004 053 469.1 filed on Nov. 03, 2004.

BACKGROUND OF THE INVENTION

The invention concerns a loop-forming nonwoven material for a mechanical closure element, in particular, for disposable hygiene articles such as various types of diapers, incontinence articles and pads, wherein a first upper side of the nonwoven material has first larger non-bonded areas which are separated from one another to form islands.

Mechanically acting closure elements, which are often called hook/loop closure elements or Velcro closure elements, are produced to have a good closing action based on engagement or hooking of the cooperating closure elements and which cannot be accidentally released from each other. On the other hand, these closure elements should be releasable when desired, i.e. without separating or tearing the materials of the closure elements. In order to prevent this, the loop-forming component of the mechanical closure element either has textile bonds or, for nonwoven materials, the fibers of the nonwoven are sufficiently solidified or bonded. Increased nonwoven solidification results in a decrease in the adhesive force of the mechanical closure system.

EP 0 870 081 B1 describes a loop-forming nonwoven material in accordance with the preamble of claim 1 which provides non-bonded island-type areas on a preferably continuous non-bonded, nonwoven fiber sheet by using calendar embossing to effect a continuous bonded region of nonwoven material between the non-bonded areas. The areas between the island-type non-bonded areas which are solidified through calendar embossing, can essentially no longer be used for adhesive bonding.

EP 1 209 271 A1 discloses a light, nonwoven material which has mutually insulated line-segment type, bonded areas and nonwoven materials with a honeycomb-shaped pattern of embossed points. WO 95/33390 discloses a nonwoven/sheet laminate, wherein a presolidified fiber nonwoven sheet is joined to an elastomeric film layer via a grid of discrete jointing points.

EP 1 048 236 A2 proposes disposition of fusion-melting, mutually parallel continuous fibers onto a fusion-melting base layer and to connect them to the base layer through straight jointing lines extending transversely to the fiber direction, thereby forming loops between the jointing lines, which may cooperate with a hook-forming component of a closure element.

It is the underlying purpose of the present invention to provide a nonwoven material which is improved in view of closing reliability and durability, thereby taking into consideration the above-mentioned target conflict in forming a loop-forming component of a mechanical closure element.

SUMMARY OF THE INVENTION

This object is achieved in accordance with the invention with a loop-forming nonwoven material of the above-mentioned type in that the first larger non-bonded areas are delimited by bonded contours and are surrounded outside of the limitation by two smaller non-bonded areas and are spaced apart from each other by these two smaller non-bonded areas.

The larger non-bonded areas are primarily available for forming a mechanically acting closing function. They are delimited or defined by a bonded contour which may be formed, in particular, through linear embossing, in particular thermal embossing, produced in particular through ultrasound welding or calendar embossing, wherein these embossing lines may be continuous or interrupted, in particular, dashed or dash-dotted lines. Further smaller non-bonded areas or fields are provided outside of this bonded contour between these first non-bonded island-type areas, which separate the first larger non-bonded areas from each other. The island-type larger areas are thereby disposed sufficiently proximate to each other, or the second smaller non-bonded areas surround bonded partial areas in such a manner, that a maximum circular surface which can be inscribed in the first larger non-bonded areas cannot fit within the second non-bonded areas.

The inventive nonwoven material provides an overall and individually projecting and sufficiently large anchoring area for the hook-forming component of the mechanical closure element in the first larger non-bonded island-type areas. The further second non-bonded areas between the island-type first non-bonded areas facilitate as continuous a mechanical connection as possible. An equally sufficient solidification of the loop-forming nonwoven material is obtained by the bonded contours which delimit the first non-bonded areas, and optionally supported by further bonded partial areas which, in turn, are surrounded by the second non-bonded areas and disposed between the first larger areas.

As mentioned above, the second smaller non-bonded areas advantageously have or, in particular, surround bonded partial areas to effect good solidity and proper embedding of the fibers of the nonwoven material. These partial areas, which may also be formed by embossing, in particular thermal embossing, may have any shape, wherein relatively short, narrow segments have proven to be advantageous for the partial areas, having a longitudinal extension of approximately two to ten times (preferably two to eight times) their width.

Each straight connecting line advantageously extends between the first larger non-bonded island-type areas through a bonded contour or a bonded partial area which is disposed between the first larger areas in order to enhance embedding of the fibers into the nonwoven material.

The bonded contours advantageously have embossing lines or embossing line sections of a width of 0.2 to 1 mm, preferably 0.2 to 0.8 mm and moreover preferably 0.3 to 0.6 mm. They advantageously have a depth of 0.4 to 1.5 mm, preferably 0.4 to 0.9 mm, preferentially 0.4 to 0.8 mm and moreover preferentially 0.5 to 0.7 mm.

The first larger non-bonded island-type areas advantageously have a dimension, in particular, a diameter of a circle inscribed in the area, of 2 to 15 mm, preferably 3 to 10 mm, preferentially 3 to 8 mm and with particular preference 4 to 7 mm.

The first larger non-bonded island-type areas advantageously have a surface portion of 5 to 75%, in particular 5 to 60%, in particular 10 to 50%, in particular 10 to 45%, in particular 15 to 45%, in particular 20 to 40%, and preferentially 30 to 40% of the overall surface of the first upper side. In accordance with the invention, it has turned out that the first larger non-bonded island-type areas may cover a relatively moderate portion of the overall surface, since the closing function is additionally supported by the smaller non-bonded areas or fields between the first larger non-bonded areas.

The shape of the first larger non-bonded island-type areas is not necessarily predetermined. Advantageously, they have a circular, oval, triangular or polygonal, preferably hexagonal or octagonal shape. These preferred structures provide an extensive anchoring area for the hook-forming component of the closure element. It turns out that the closing function is particularly effective through relatively large island-type areas having dimensions which are preferably identical in all directions, as is the case with a circle or regular polygon, in particular, hexagon.

In one particularly suitable arrangement of the first island-type areas, these areas have a mutual separation from each other of at least 1 mm, preferably at least 1.5 mm, in particular at least 2 mm and preferentially at least 2.5 mm and with particular preference at least 3 mm. They have, however a maximum separation of preferably maximally 10 mm, in particular maximally 5 mm.

One can obtain good and sufficient stability of the nonwoven material, i.e. good embedding of the fibers and thereby great solidity of the nonwoven material when the overall surface portion of bonded areas is preferably 10 to 60%, preferably 15 to 40%, furthermore preferably 15 to 30%, in particular 15 to 25% and preferentially 19 to 22% of the overall area of the first surface. Bonded areas in this connection mean bonded contours which delimit the first island-type areas and also optionally additional bonded partial areas between the first island-type areas.

The inventive nonwoven material may preferably comprise a spunbonded material or a card web or a meltblown nonwoven or a water-needled nonwoven material. It may also advantageously be a nonwoven laminate which consists of several nonwoven layers. In accordance with a preferred embodiment of the invention, the material comprises a spunbonded material and a card web which are connected to each other. In this case, the card web advantageously forms the first upper side and constitutes a landing zone for a hook-forming component of a mechanical closure element.

When the inventive hook-forming nonwoven material consists of several nonwoven layers, i.e. is a nonwoven laminate, these layers are advantageously connected to each other through applying the bonded contours delimiting the first larger non-bonded island-type areas. This may be realized e.g. by thermo embossing, in particular, by calendar embossing or ultrasound welding. When the inventive nonwoven material is formed as a nonwoven laminate, a nonwoven layer facing away from the first upper side may be solidified by a further bonding pattern generated, in particular, through thermo embossing, in order to increase the overall solidity. This further nonwoven layer thus does not form the landing zone for a hook-forming component of the closure element but is provided on the side facing away. The bonding pattern is preferably mounted during previous production of the further nonwoven layer to pre-solidify it.

The surface density of an inventive non-woven material is preferably 15 to 120 g/m², in particular 20 to 90 g/m², in particular 30 to 80 g/m², in particular 40 to 70 g/m², and preferentially 50 to 65 g/m².

The surface density of the nonwoven layer which forms the first upper side and has the first nonbonded island-type areas, the bonded contours and the second non-bonded areas is preferably 10 to 60 g/m², in particular 10 to 40 g/m², in particular 15 to 35 g/m², and moreover in particular 20 to 35 g/m².

The above-mentioned surface densities in connection with the claimed design of the first upper side produce nonwoven materials which do not only ensure good closing function in cooperation with a hook-forming component of a closure element but also have good mechanical properties, in particular, in view of comfortable flexibility, and however also assume a supporting function. This means that these nonwoven materials can be used, in particular, as a belt in absorbent hygiene articles.

In view of the design of the nonwoven material, the nonwoven layer which forms the first upper side advantageously and suitably has fibers of a thickness of 1 to 10 dtex, preferably 2 to 8 dtex and preferably 3 to 6 dtex or consists of such fibers. In another advantageous fashion, the nonwoven layer which forms the first upper side comprises hydrophilic fibers or consists of hydrophilic fibers.

When the inventive nonwoven material consists of several nonwoven layers, it may comprise one nonwoven layer as a carrier which has a surface density of 10 to 100 g/m², preferably 15 to 60 g/m², and moreover preferably 30 to 40 g/m². This carrier layer faces away from the first upper side. It advantageously comprises fibers of a thickness of 1 to 6 dtex, preferably 1 to 4 dtex and moreover preferably 2 to 4 dtex.

In a particularly advantageous further development of the invention, the nonwoven material is breathable, i.e. permeable to water and/or air. This improves the comfort of wear, in particular, when the nonwoven material is used as a belt for absorbent hygiene articles.

As is mentioned above, the inventive nonwoven material advantageously has a stiffness of <0.80 N in particular <0.60 N, in particular <0.40 N, in particular <0.30 N, in particular <0.25 N, in particular <0.2 N, in particular <0.18 N, and moreover in particular <0.16 N, however at least 0.05 N. This stiffness is determined in accordance with the test method described in EP 0 699 066 B1 of the modified version of the test ASTM D 4032-82 CIRCULAR BEND, the disclosure of which and the relevant content of EP 0 699 066 B1 are hereby explicitly incorporated by reference. In addition thereto, this test method is further specified, such that in the test arrangement the first upper side of the nonwoven laminate is disposed at the bottom, i.e. forms that surface which faces away from the punch of the test apparatus.

A further subject matter of the present invention is a disposable hygiene article, in particular different types of diapers, incontinence diapers or pads, which is characterized by a mechanical closure element which comprises or is formed of a loop-forming nonwoven material in accordance with any one or more of the claims 1 through 24.

In such a hygiene article, the female Velcro fastener closure component of a conventional disposable diaper (see WO95/33390) may comprise or consist of this inventive nonwoven material.

Such a hygiene article may also comprise a belt that can be closed on top of itself and extends in the peripheral direction of the hip of a user. This belt forms a closed hip opening, and a main part having the absorbing components of the hygiene article is pulled from between the legs of a user when applying the article, and preferably detachably fixed to the previously closed belt.

In another particularly important embodiment of the invention, the belt is formed from a preferably one-piece material section, wherein the material section comprises or is formed of a non-woven material in accordance with one or more of the claims 1 through 24.

This is advantageous in that the belt extends in the peripheral hip direction by 25 to 200 cm, in particular 40 to 180 cm, in particular 60 to 180 cm, in particular 100 to 180 cm and moreover 120 to 180 cm.

In another advantageous fashion, the belt or hook-forming component, which is formed by an inventive non-woven material, extends in the longitudinal direction of the hygiene article by 3 to 20 cm, in particular 3 to 15 cm, in particular 4 to 10 cm and moreover, in particular, 4 to 6 cm.

The invention also concerns a hygiene article, wherein the loop-forming nonwoven material cooperates with a hook-forming component of a mechanical closure element for closing the hygiene article, such that an adhesive force as shearing force of at least 5 N/25 mm and at most 80 N/25 mm is achieved. Preferred ranges are stated in the claims.

In this connection, reference is made to the fact that the invention also concerns a mechanical closure element for use in absorbent hygiene articles whose loop-forming component comprises or consists of an inventive nonwoven material.

Figure 4:
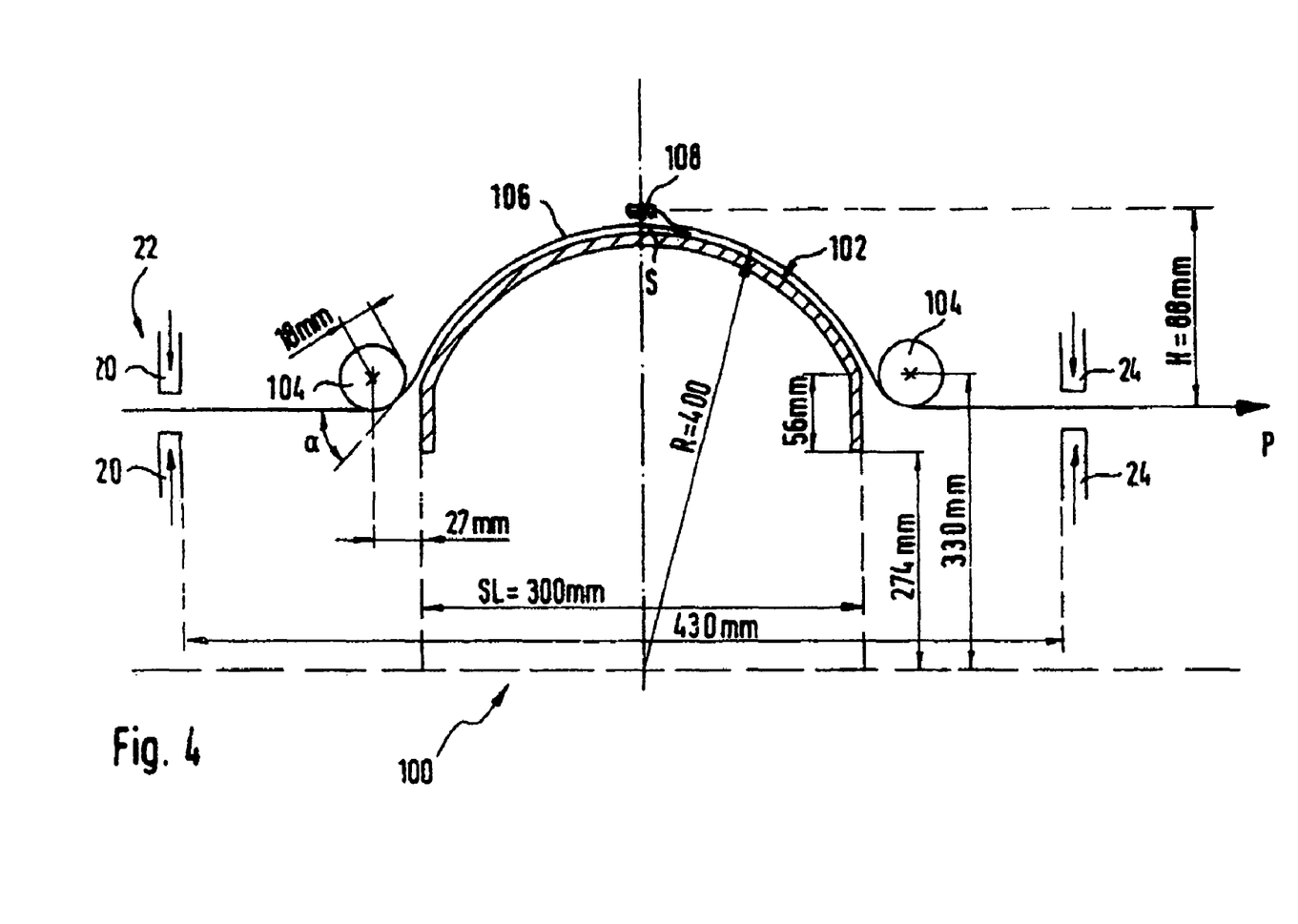
FIG. 4 shows a schematic view of the structure of a tension test with a device with curved surface.

A test method for determining the closing forces under shearing stress is described below. A tension testing machine of the type Z010/TN 2S, measuring load 100 N, available from the company Zwick GmbH & Co KG, Ulm, Germany can be used to perform the test method, which has a clamping jaw width for clamping the sample of 60 mm. For performing the test method, the tested closing system with loop-forming component and hook-forming component which adheres thereto, is disposed over a curved surface which simulates the curvature of the belly area of a user (FIG. 4). The closure element is connected to the clamping jaws of the tension testing machine by a flexible substrate, e.g. an adhesive tape, which is adhesive on one side, of a preferred width of 25 mm, available under the trade name STA 306 from the company 3M Deutschland GmbH in Neuss. The adhesive tape is made of polypropylene, its surface is coated with a urethane-modified silicon polymer. The surface density of the adhesive application is 23 g/m$^2$. The sample disposed over the curved surface and consisting of planar sections of the closure element, which are disposed on top of each other in an adhesive fashion, is tensioned by the tension testing machine to exert shearing stress onto the adhering planar sections.

Preparation of the Sample:

The mechanical closure elements to be used, i.e. the loop-forming nonwoven material 106 and a hook-forming component 108 of the closing system are conditioned for 24 h at 23° C. and 50% relative air humidity. Samples of a size of 50×300 mm are punched out of the loop-forming nonwoven material and disposed or fixed like a sandwich in the center between the ends of two one-sided adhesive tapes 101 of a width of 25 mm, which are glued against each other, such that the nonwoven material projects by 50×250 mm (FIGS. 5a, 5b).

Figure 5A:
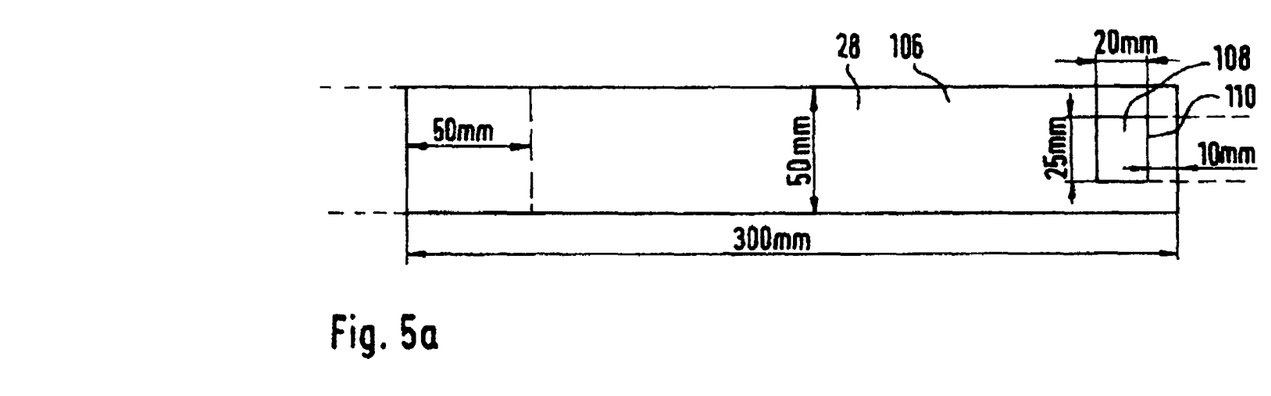
FIGS. 5a-d show schematic views of the sample.
Figure 5B:
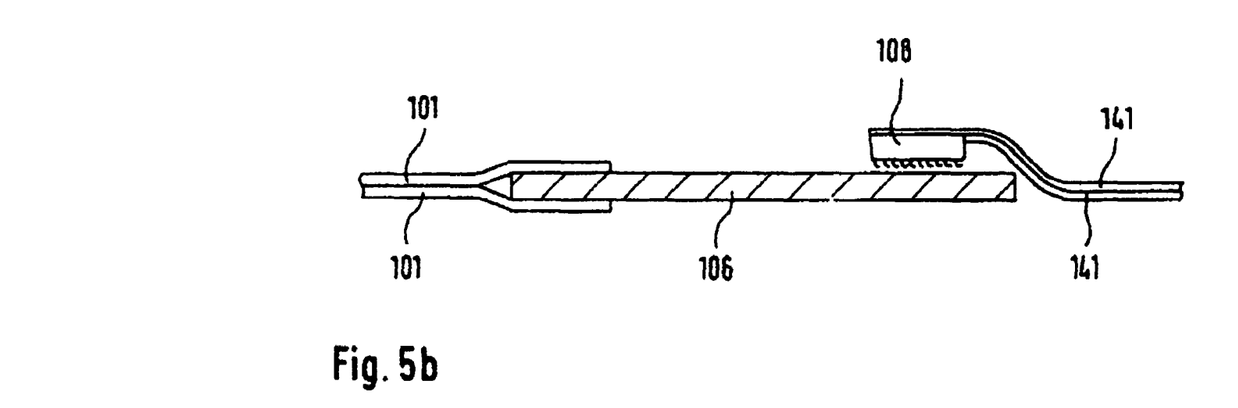

In the same fashion, a planar section of 25×20 mm is punched out of the hook-forming component 108 of the closure element and fixed by two tapes 141, which are adhesive on one side and are glued to each other with their sticking sides, such that the upper adhesive tape covers the rear side of the planar section and the lower adhesive tape abuts flush with the planar section (FIGS. 5a and 5b).

The planar section of the hook-forming component 108 is now disposed onto the hook-forming nonwoven material 106, wherein the separation from the longitudinal end edge of the nonwoven material is 10 mm and from each lateral longitudinal edge 12.5 mm (FIG. 5a).

Figure 5C:
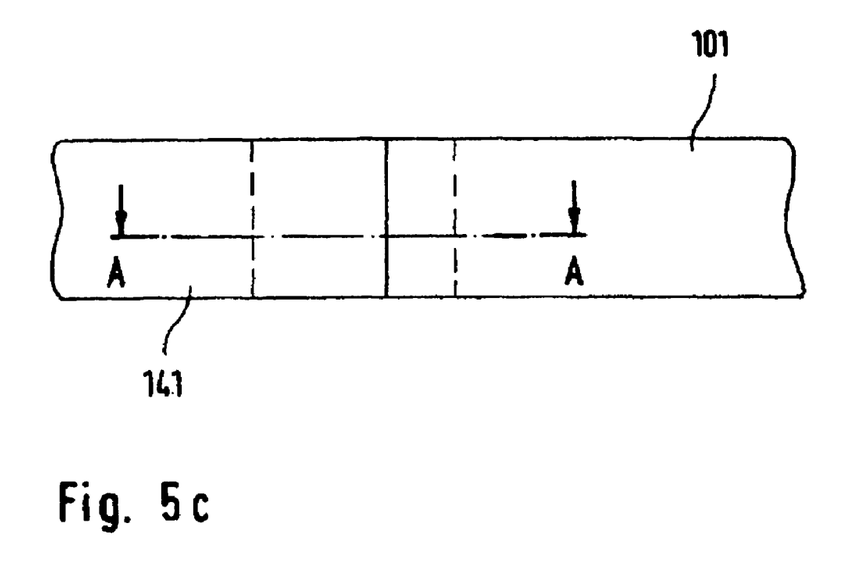
Figure 5D:
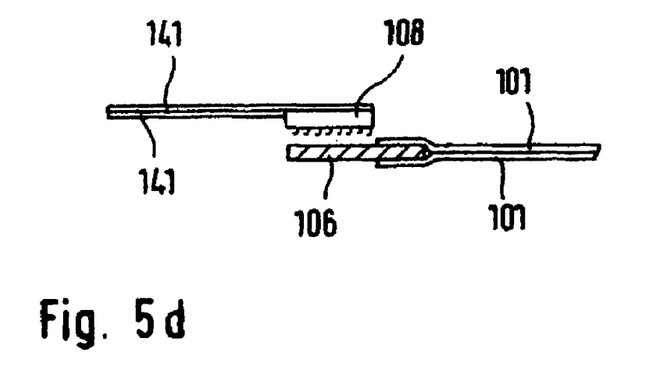

When the original, available loop-forming nonwoven material 106 is smaller and it is not possible to provide a sample of a size of 50 mm×300 mm, the size of the sample is selected to be 25 mm×30 mm and this section is disposed or fixed like a sandwich in the center between the ends of two one-sided adhesive tapes 101 described in more detail above, of a width of 25 mm, which are glued to each other, such that the nonwoven material projects by 25×20 mm (FIGS. 5c, 5d). In this case, the sections of the hook-forming component 108 and the loop-forming nonwoven material 106, prepared in this fashion, are disposed on top of each other over their full surface (FIGS. 5c, 5d).

The planar sections disposed on top of each other in this fashion or as described above, are connected to each other by rolling four times using a roll which is 50 mm wide and has a diameter of 100 mm with smooth surface and a weight of 5 kg, wherein the rolling speed is 20 to 100 mm/sec.

Test Method

The loop-forming nonwoven material extended as described above is centered and clamped in the lower clamping jaw of the tension testing machine, and the opposite end of the hook-forming component extended as described above is clamped in a centered position into the movable upper clamping jaw of the tension testing machine.

Figure 6:
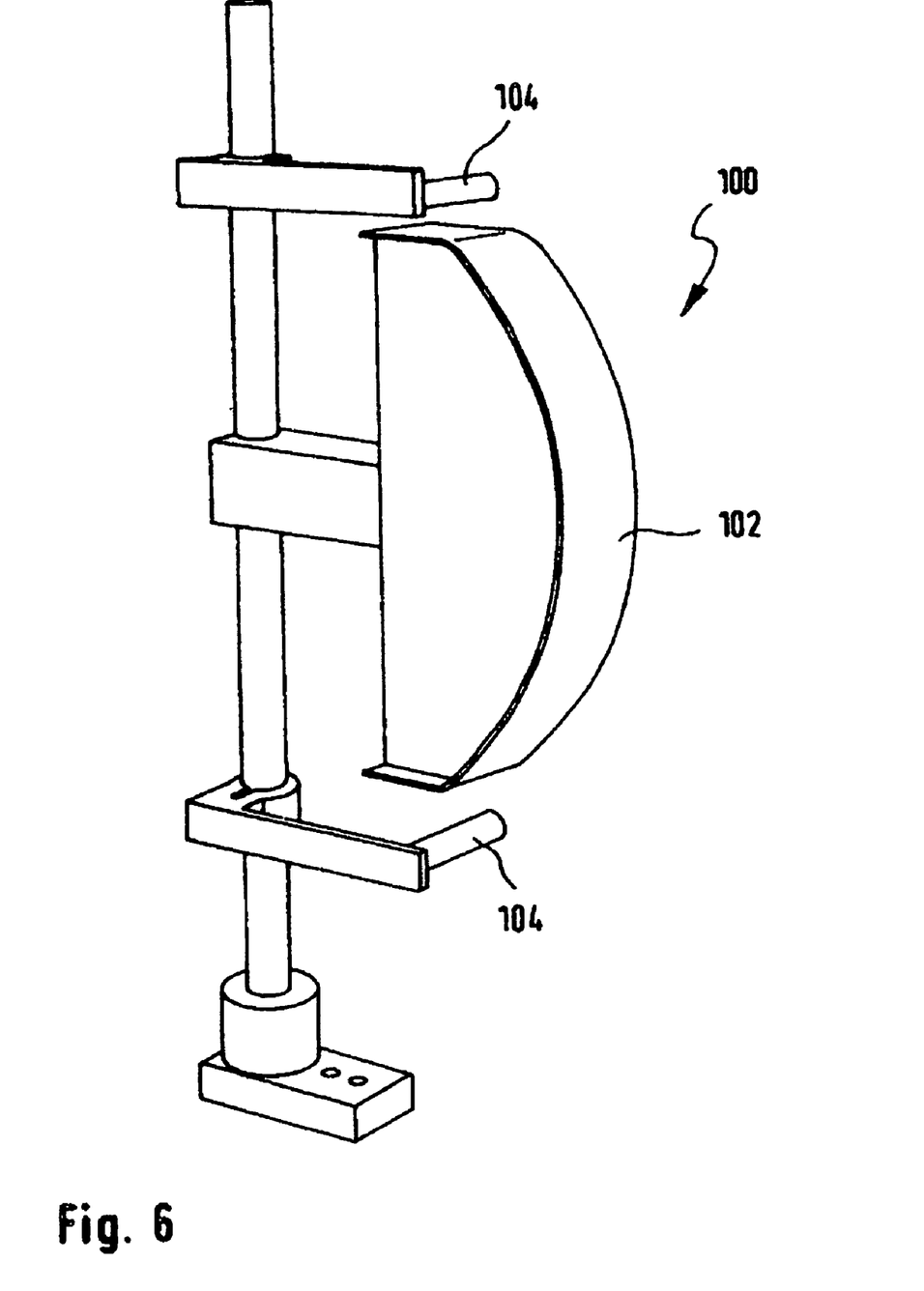
FIG. 6 shows a perspective view of the device of FIG. 4.

The clamped sample is disposed over the device 100 shown in FIGS. 4, 6 which simulates the belly or hip area of a user. This device 100 is shown in perspective view in FIG. 6. It shows an arcuately curved surface 102 of polished steel with a roughness height of 5 to 25 µm and with a radius of curvature R of 400 mm at least in sections and a chord length SL of 300 mm. Deflection rollers 104 are moreover provided above and below the curved surface 102, having a diameter of 18 mm, which deflect the sample disposed on the curved surface, in a vertical direction by H=88 mm, where it is connected to clamps 20, 24 of the tension testing device (not shown). It is deflected through an angle α of 60°. This keeps the withdrawal angle substantially tangential to the curved surface and also constant. The planar sections 106, 108 disposed on top of each other of the components of the closure element are positioned relative to the curve surface 102, such that the hook-forming component comes to rest in the center in the vertex S of the curved surface 102.

The movable clamp 24 to which the hook-forming component is connected, is then moved with the test speed (as stated below) in the direction of arrow P and the tensile force between the clamps is thereby determined. The test parameters are:

| | |
|---|---|
| Test speed: | 300 mm/min |
| Clamping length of the sample | 430 mm (see FIG. 4) |
| Measuring path: | distance until detachment of the closure element component n |
| Pre-force: | 0.2 N |
| Test number: | n ≧ 6 |

In the evaluation, the maximum force determined before the closure elements become detached, rounded to two decimal points in N (Newton), is noted and stated in the form of an average value of the n measurements and the standard deviation and a minimum value and a maximum value.

Figure 7:
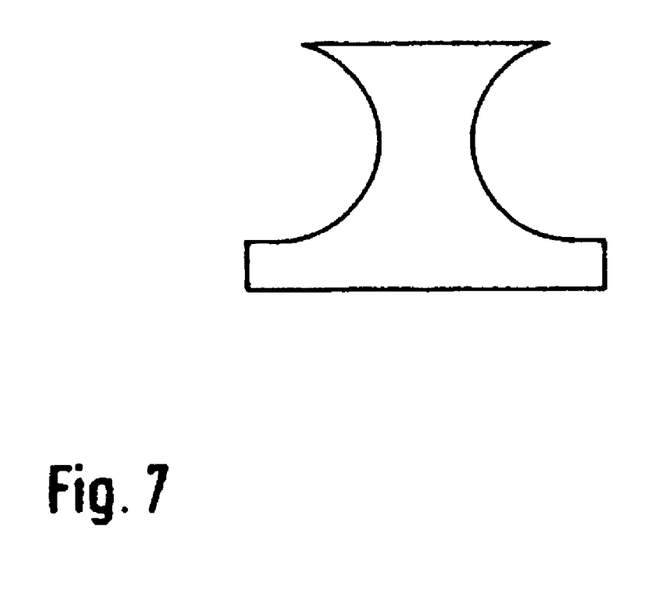
FIGS. 7 and 8 show views of a hook-forming component of a closure element.
Figure 8:
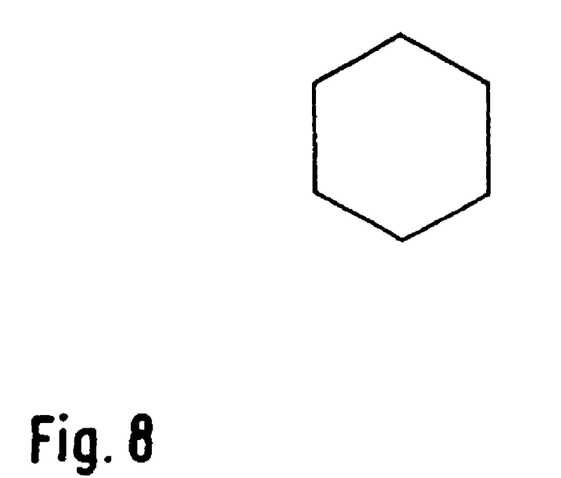

A hook-forming component which can be used together with the inventive nonwoven material as a loop-forming component of a mechanical closure element is shown e.g. under the trade name "Microplast" 42-288-HX200-PP3 by the company G. Binder GmbH & Co. KG Textil- und Kunststofftechnik, Holzgerlingen, Germany. FIGS. 7 and 8 show illustrations of the shape of the hook-forming component. The hooks have a mushroom shape with approximately hexagonal head surface. There are approximately 288 such mushroom shaped projections per cm$^2$. The material consists of polypropylene and has a thickness of approximately 0.42 mm. It was produced through extrusion. The height of the mushroom-shaped elevations from the base of the material is approximately 0.26 mm. The separation between the edges of the heads is approximately 200 µm.

BRIEF DESCRIPTION OF THE DRAWING

Further features, details and advantages of the invention can be extracted from the claims, the drawing, and the following description of a preferred embodiment of the invention.

FIG. 2 shows a schematic sectional view of the non-woven material of FIG. 3a;

FIG. 3b shows a sectional view (detail) of FIG. 3a;

DESCRIPTION OF THE PREFERRED EMBODIMENT

Figure 1:
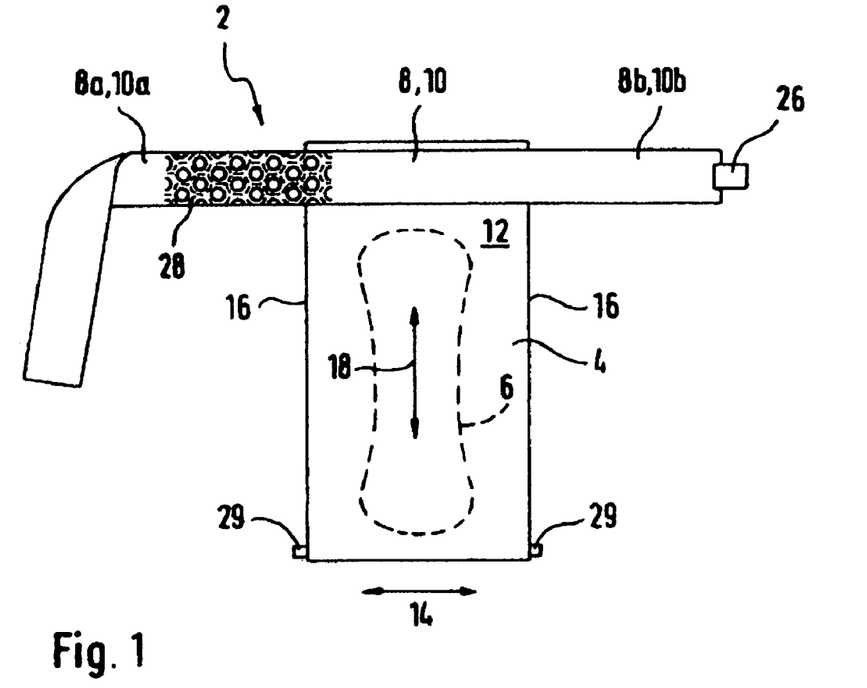
FIG. 1 shows a schematic view of an inventive hygiene article with a belt of an inventive nonwoven material.

FIG. 1 schematically shows a disposable belt diaper 2 with a main part 4 and an indicated absorption body 6. A one-piece material section 8 is joined to the main part 4, which forms a hip belt 10 of the hip diaper. FIG. 1 shows the belt in the unfolded state. The one-piece material section 8 is undetachably joined to an outer side 12 of the main part 4. It extends in the transverse direction 14 of the belt diaper 2 via lateral longitudinal edges 16 in the unfolded state, through at least 300 mm, in particular at least 400 mm, in particular at least 500 mm, in particular at least 600 mm, in particular at least 700 mm in each case. In FIG. 1, the first material section 8a is considerably longer than the second material section 8b, i.e. the extension of the first hip belt section 10a in the unfolded state in the transverse direction 14 beyond the longitudinal edge 16 of the main part 4 is larger by preferably 100 mm, preferably 200 mm, and preferentially 300 mm than that of the second hip belt section 10b.

The first and second material sections may also have the same length.

A closure element 26 is also provided at the end of the second hip belt section 10b, having the shape of a shackle 26 with mechanical closure elements, which may cooperate in a detachable adhesive fashion with counter closure elements on the first hip belt section 10a, in particular with its total outer surface, when the hip belt 10 is closed to form a hip opening which is closed in the peripheral hip direction. The outer side of the hip belt advantageously comprises an inventive loop-forming nonwoven material which forms the counter closure elements. This loop-forming nonwoven material is schematically indicated with reference numeral 28 only over a limited length of the first hip belt section. In accordance with a preferred embodiment of the invention, the hip belt consists of this nonwoven material 28, such that the loop-forming component of the nonwoven material forms the overall outer side of the hip belt.

For applying the belt diaper 2, the hip belt 10 is closed on top of itself and the main part 4 is subsequently pulled from between the legs of a user and detachably fixed via further shackles 29, comprising mechanical closure elements, on both sides of the main part 4 on the hip belt 10.

Figure 2:
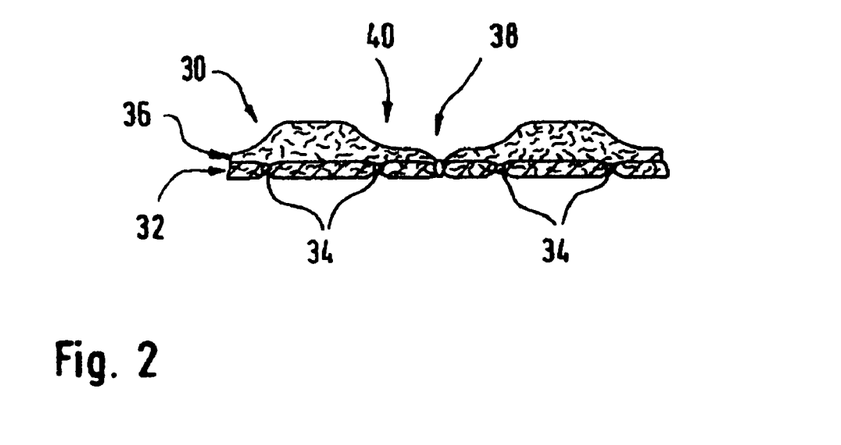
Figure 3A:
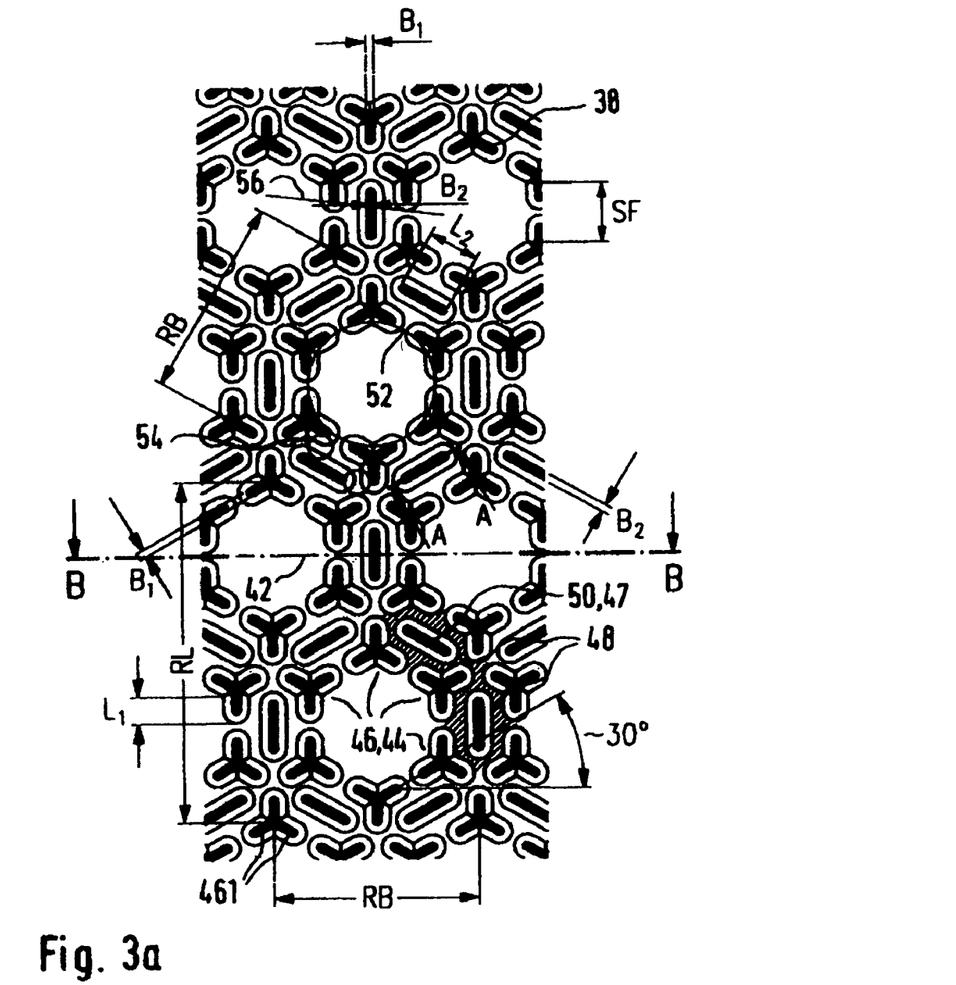
FIG. 3a shows a top view of the surface, in unwound flat projection, of an engraving roller for embossing the inventive non-woven material, and also a schematic view of the first upper side of the nonwoven material.

The nonwoven material 28 consists of a nonwoven laminate 30 which is schematically shown in the sectional view of FIG. 2. The section thereby extends along a line B-B shown in FIG. 3a. It has a polypropylene spunbonded layer 32 consisting of fibers of a fiber thickness of 2.2 dtex with a surface density of 30 g/m$^2$ as a carrier, which is presolidified by oval bonding points 34 of a surface density of 48.37 points/cm$^2$ (thermal embossing points), wherein the dimensions of the semi-axes of the oval bonding points are 0.85 mm and 0.59 mm in each case, and the pressing surface of the oval bonding points is accordingly 0.394 mm$^2$ and the portion of the bonding points of the overall surface is thus 19.0%. The depth of the bonding points is 0.80 mm. A card web layer 36 is joined to this spunbonded layer 32 through hot calendar embossing. In the illustrated case, the card web consists of hydrophilized polypropylene fibers of a thickness of 4.4 dtex and a fiber length of 40 mm. FIG. 3 shows a view of the "unwound" surface of a calendaring roller which corresponds to an embossing pattern 38 disposed onto the first upper side 40 of the card web layer 36 through hot calendaring. FIG. 3 also schematically shows a view of the first upper side 40 of the nonwoven laminate 30.

First larger nonbonded areas 42 are formed on the first upper side 40 of the nonwoven laminate 30 through applying an embossing pattern 38, which are limited by a thermally bonded contour 44 of interrupted first segments 46. In the present case, these first segments 46 have a regular trilobal shape when viewed from above. The arms 461 of these first segments 46 have a length L1 of 1.04 mm and a width B1 of 0.47 mm. The limited first nonbonded areas are hexagonal and are disposed at mutual separations like islands on the first upper side 40. Second nonbonded areas 48 are located between the first areas 42, which are smaller than the first nonbonded areas 42. These second nonbonded areas, in turn, surround bonded partial areas 50 which are formed like bars by second segments 47. These second segments 47 have a length L2 of 2.07 mm and a width B2 of 0.47 mm. The embossing depth of the first and second segments is 0.59 mm in each case. In the shown example, the sides of the hexagon of the first non-bonded island-type areas have dimensions SF of 2.9 mm. Their separation is approximately 2.6 mm.

In particular, it is not possible to dispose a maximum size circle 52 inscribed in the first larger areas 42, having a diameter of 4.8 mm in the present case, within the second, nonbonded smaller areas 48. The maximum size circles 54 are indicated therein.

The pattern repeat (RB) of the embossing pattern 38 is 8 mm, the pattern repeat length RL is 13.86 mm.

The overall surface portion of bonded areas 44, 50 is 20.7%. The surface portion of the first larger nonbonded island-type areas (42) is approximately 35.7%, wherein the size of the surface of the inscribed circle 52 is used to determine the surface of a first nonbonded island-type area.

The shearing force determined in accordance with the above-described test method of this nonwoven material is 51.00 N/25 mm, wherein the material "Microplast" 42-288-HX200-PP3 by the company G. Binder GmbH & Co. KG Textil- und Kunststofftechnik, Holzgerlingen, was used as the Velcro hook component.

The rigidity of the nonwoven material determined in accordance with the test method disclosed in EP0699066B1 is 0.13 N, wherein in the test arrangement the spunbonded side is at the top, i.e. forms the surface which faces the punch of the test apparatus.

In a further embodiment of the present invention, only the surface density of the spunbonded material was increased to 45 g/m² and the embossing pattern 38 connecting the non-woven materials was modified:

Length L1 of the arms 461 of the first segments 46: 1.0 mm
Width B1 of the arms 461 of the first segments 46: 0.4 mm
Length L2 of the second segments: 47: 2.0 mm
Width B2 of the second segments 47: 0.4 mm
Surface portion of bonded areas: 17.1%
Embossing depth of the first and second segments: 0.68 mm The shearing force determined in accordance with the above-described test method of this further embodiment is 58.89 N/25 mm, wherein the material "Microplast" 42-288-HX200-PP3 by the company G. Binder GmbH & Co. KG Textil- und Kunststofftechnik, Holzgerlingen, was used again as the Velcro hook component.

The rigidity of this further nonwoven material determined in accordance with the test method disclosed in EP0699066B1 is 0.28 N, wherein, in the test arrangement, the spunbonded side is at the top, i.e. forms the surface which faces the punch of the test apparatus.

Each straight connecting line 56 between neighboring first larger areas 42 extends always through a bonded contour 44 or a bonded partial area 50 which is disposed between the first larger areas 42.

Figure 3B:
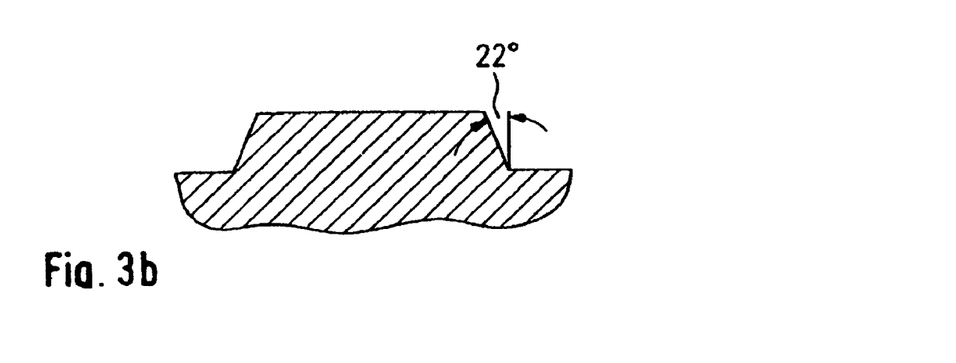

FIGS. 3a and 3b show preferred and exemplary dimensions of the embossing structure 38, wherein FIG. 3b shows a section along line A-A through a second segment 56.

We claim:

1. A mechanically acting closure element in disposable hygiene articles, diapers, incontinence articles, having a loop-forming component and a hook-forming component, the loop-forming component being a loop-forming nonwoven material comprising:
   First nonbonded areas disposed in an upper side of the non-woven material, said first nonbonded areas being spaced apart from each other and disposed like islands; bonded contours delimiting said first nonbonded areas; and second nonbonded areas disposed outside of said bonded contours, said second nonbonded areas being smaller than said first nonbonded areas and separating adjacent first nonbonded areas from each other, wherein a straight line extending between adjacent first non-bonded areas always intersects a bonded contour or a bonded partial area which is disposed between said first adjacent nonbonded areas, said first nonbonded areas having a surface portion of 20 to 45% of an overall surface of said upper side, wherein an overall surface portion of bonded areas is 10 to 60% of an overall area of said upper side,
   Wherein said first non-bonded areas have a dimension or a diameter of a circle inscribed inside said nonbonded first areas of 3 to 15 mm,
   Wherein all of said first nonbonded areas have a maximum mutual separation from adjacent ones of said first non-bonded areas of 10 mm,
   Wherein the loop-forming nonwoven material cooperates with a hook-forming component of a mechanical closure element for closing the hygiene article, such that an adhesive force as a shearing force of at least 5 N/25 mm but at most 80 N/25mm is achieved.

2. The closure element of claim 1, wherein said second nonbonded areas have bonded partial areas or bonded partial areas which they surround.

3. The closure element of claim 1, wherein said bonded contours have embossing lines or embossing line sections of a width of 0.2 to 1 mm, 0.2 to 0.8 mm, or 0.3 to 0.6 mm.

4. The closure element of claim 1, wherein said bonded contours have embossing lines or embossing line sections of a depth of 0.4 to 1.5 mm, 0.4 to 0.7 mm, or 0.5 to 0.7 mm.

5. The closure element of claim 1, wherein said first non-bonded areas have a dimension or a diameter of a circle inscribed inside said nonbonded first areas of 3 to 8 mm.

6. The closure element of claim 1, wherein said first non-bonded areas have a circular, oval, triangular, polygonal, or hexagonal shape.

7. The closure element of claim 1, wherein said first non-bonded area have a mutual separation from adjacent ones of said first nonbonded areas of at least 1 mm, at least 1.5 mm, at least 2 mm, at least 2.5 mm or at least 3 mm.

8. The closure element of claim 1, wherein said first non-bonded areas have a maximum mutual separation from adjacent ones of said first nonbonded areas of 5 mm.

9. The closure element of claim 1, wherein the material comprises a spunbonded material, a card web, a meltblown nonwoven, or a water-needled nonwoven material.

10. The closure element of claim 1, wherein the nonwoven material comprises a nonwoven laminate, said nonwoven laminate comprises a spunbonded material and a carded web which are connected to each other, which are connected to each other through thermo embossing, or which are connected to each other through hot calendar embossing.

11. The closure element of claim 10, wherein a carded web forms said upper side to define a landing zone for a hook-forming component of a mechanical closure element.

12. The closure element of claim 1, wherein layers of nonwoven laminate are connected to each other through thermal bonding when applying said bonded contours limiting said first nonbonded areas.

13. The closure element of claim 1, wherein a nonwoven layer facing away from said first upper side is solidified by a further bonding pattern.

14. The closure element of claim 1, wherein the material has a mass per unit area of 15 to 120 g/m², 20 to 90 g/m², 30 to 80 g/m², 40 to 70 g/m², or 50 to 65 g/m².

15. The closure element of claim 1, wherein a nonwoven layer which forms said upper side, comprises hydrophilic fibers or consists of hydrophilic fibers.

16. The closure element of claim 1, further comprising a further nonwoven layer as a carrier which has a mass per unit area of 10 to 100 g/m², 15 to 60 g/m², or 30 to 40 g/m².

17. The closure element of claim 16, wherein said further nonwoven layer has or consists of fibers of a thickness of 1 to 6 dtex, 1 to 4 dtex, or 2 to 4 dtex.

18. The closure element of claim 1, wherein the material has a stiffness of <0.80 N, <0.60 N, <0.40 N, <0.30 N, <0.25 N, <0.20 N, <0.18 N, <0.16 N but at least 0.05 N.

19. The closure element of claim 1, wherein the closure element is a hip belt of a hygiene article that extends in a peripheral direction of the hip of a user and can be closed onto itself.

20. The closure element of claim 19, wherein said hip belt consists essentially of the loop-forming nonwoven material.

21. The closure element of claim 19, wherein the nonwoven material extends in a peripheral hip or transverse direction of the hygiene article by 25 to 200 cm, 40 to 180 cm, 60 to 180 cm, 100 to 180 cm or 120 to 180 cm.

22. The closure element of claim 19, wherein the nonwoven material extends in a longitudinal direction of the hygiene article by 3 to 20 cm, 3 to 15 cm, 4 to 10 cm or 4 to 6 cm.

23. The closure element of claim 1, wherein the loop-forming nonwoven material cooperates with the hook-forming component of a mechanical closure element for closing the hygiene article, such that an the adhesive force as a shearing force of at least 10 N/25 mm or at least 15 N/25mm or at least 20 N/25mm or at least 25 N/25mm or at least 30 N/25mm or at least 35 N/25 mm or at least 40 N/25 mm or at least 45 N/25 mm or at least 50 N/25 mm is achieved.

24. The closure element of claim 1, wherein the loop-forming nonwoven material cooperates with a hook-forming component of a mechanical closure element for closing the hygiene article, such that an adhesive force as a shearing force of at most 70 N/25 mm is achieved.

25. The closure element of claim 1, wherein the overall surface portion of bonded areas is 15-40%, or 15-30%, or 15-25%, or 19-22% of an overall area of said upper side.

* * * * *